United States Patent [19]
Brown

[11] Patent Number: 5,316,010
[45] Date of Patent: May 31, 1994

[54] APPARATUS FOR NONINVASIVE MEASURING OF UPPER AIRWAY RESISTANCE IN HUMANS DURING SLEEP

[76] Inventor: Jesse P. Brown, 708 Westcott St., Syracuse, N.Y. 13210

[21] Appl. No.: 42,279

[22] Filed: Apr. 2, 1993

[51] Int. Cl.$^5$ .............................. A61B 5/085
[52] U.S. Cl. ................... 128/720; 128/721; 73/655
[58] Field of Search ............. 128/720, 721, 665, 666, 128/664, 667, 675, 782; 33/DIG. 3, DIG. 13; 73/705, 655, 774, 775; 250/227.21, 231.19, 208.4; 356/4, 373; 84/724; 341/31; 361/173; 340/574, 575

[56] References Cited

U.S. PATENT DOCUMENTS

| | | | |
|---|---|---|---|
| 3,483,861 | 12/1969 | Tiep | 128/721 |
| 3,913,563 | 10/1975 | Ball | 73/655 |
| 4,180,059 | 12/1979 | Tiep | 128/721 |
| 4,696,307 | 9/1987 | Montgieux | 128/782 |
| 4,777,962 | 10/1988 | Watson et al. | 128/716 |
| 4,787,396 | 11/1988 | Pidorenko | 128/667 |

Primary Examiner—Richard J. Apley
Assistant Examiner—John Mulcahy
Attorney, Agent, or Firm—Homer Smith

[57] ABSTRACT

An apparatus for measuring changes in intrathoracic pressure and upper airway resistance which occurs in humans during sleep and includes a photoelectric plethysmographic transducer associated with the suprasternal fossa to measure movement of the skin surface which correlates with changes in intrathoracic pressure and upper airway resistance. The transducer includes a housing having a flexible diaphragm bonded to the skin surface at the suprasternal fossa. A photodiode is mounted on the diaphragm within the housing and a light emitting diode is mounted within the housing in spaced relation to the photodiode. The housing is fixedly secured in position whereby movement of the skin surface varies the output voltage of the photodiode which provides a signal that enables measurement of changes in intrathoracic pressure and upper airway resistance in humans during sleep.

3 Claims, 1 Drawing Sheet

5,316,010

APPARATUS FOR NONINVASIVE MEASURING OF UPPER AIRWAY RESISTANCE IN HUMANS DURING SLEEP

FIELD OF THE INVENTION

This invention relates to an apparatus for measuring changes in intrathoracic pressure and upper airway resistance which occurs in humans during sleep and includes a photoelectric plethysmographic transducer associated with the suprasternal fossa to measure movement of the skin surface which correlates with changes in intrathoracic pressure secondary to upper airway resistance. The transducer includes a housing having a flexible diaphragm bonded to the skin surface at the suprasternal fossa. A photodiode is mounted on the diaphragm within the housing and a light-emitting diode is mounted within the housing in spaced relation to the photodiode. The housing is fixedly secured in position, whereby movement of the skin surface varies the output voltage of the photodiode, providing a signal that enables measurement of changes in intrathoracic pressure and upper airway resistance in humans during sleep.

DESCRIPTION OF THE PRIOR ART

Various procedures have been developed and apparatuses devised to monitor respiration and detect apnea, which, in adults, can assist in the diagnosis of upper airway resistance or obstructions. Typical of such devices are respiration monitors associated with the nostrils as disclosed in the following U.S. Pat. Nos.:
2,831,181
2,232,288
4,777,963
4,878,502

In addition, various efforts have been made to provide a noninvasive method of monitoring intrathoracic pressure. One effort, based on respiratory inductive plethysmography involved the detection of changes in inductance within a flat coil of wire adhered to the suprasternal fossa to estimate intrathoracic pressure. Another effort involved the use of a pressure capsule adhered at the site of the suprasternal fossa to estimate intrathoracic pressure. In each case, the methodology was developed to calculate dynamic lung compliance in humans during resting wakefulness. Neither method gained wide acceptance because of inherent postural/movement artifacts. In addition, the respiratory inductive plethysmography method required modification of the calibrator/demodulator unit which resulted in greater expense than justified by the results. The prior art has not suggested the present invention which involves the use of a noninvasive photoelectric plethysmographic transducer for measuring changes in intrathoracic pressure and upper airway resistance in humans during sleep.

SUMMARY OF THE INVENTION

An object of the present invention is to provide an apparatus and method of measuring changes in intrathoracic pressure and upper airway resistance in humans during sleep by utilizing a noninvasive transducer having a movable component adhered to the skin surface at the suprasternal fossa of a human to produce a signal that is a function of the magnitude of movement of the skin surface which increases during episodes of increased upper airway resistance during sleep.

Another object of the invention is to provide a transducer in accordance with the preceding object which includes a rigid housing having an open bottom area closed by a rubber diaphragm adhered to the skin surface at the suprasternal fossa to measure movement of the skin surface.

A further object of the invention is to provide a photodiode on the inner surface of the diaphragm and a light source in the form of a light emitting diode facing the photodiode whereby movement of the photodiode in relation to the light source varies the output voltage of the photodiode as a function of the movement of the skin surface to produce a signal to measure changes in intrachoracic pressure and upper airway resistance in a human during sleep.

These together with other objects and advantages which will become subsequently apparent reside in the details of construction and operation as more fully hereinafter described and claims, reference being had to the accompanying drawings forming a part hereof, wherein like numerals refer to like parts throughout.

DESCRIPTION OF THE PREFERRED EMBODIMENT

Figure 1:
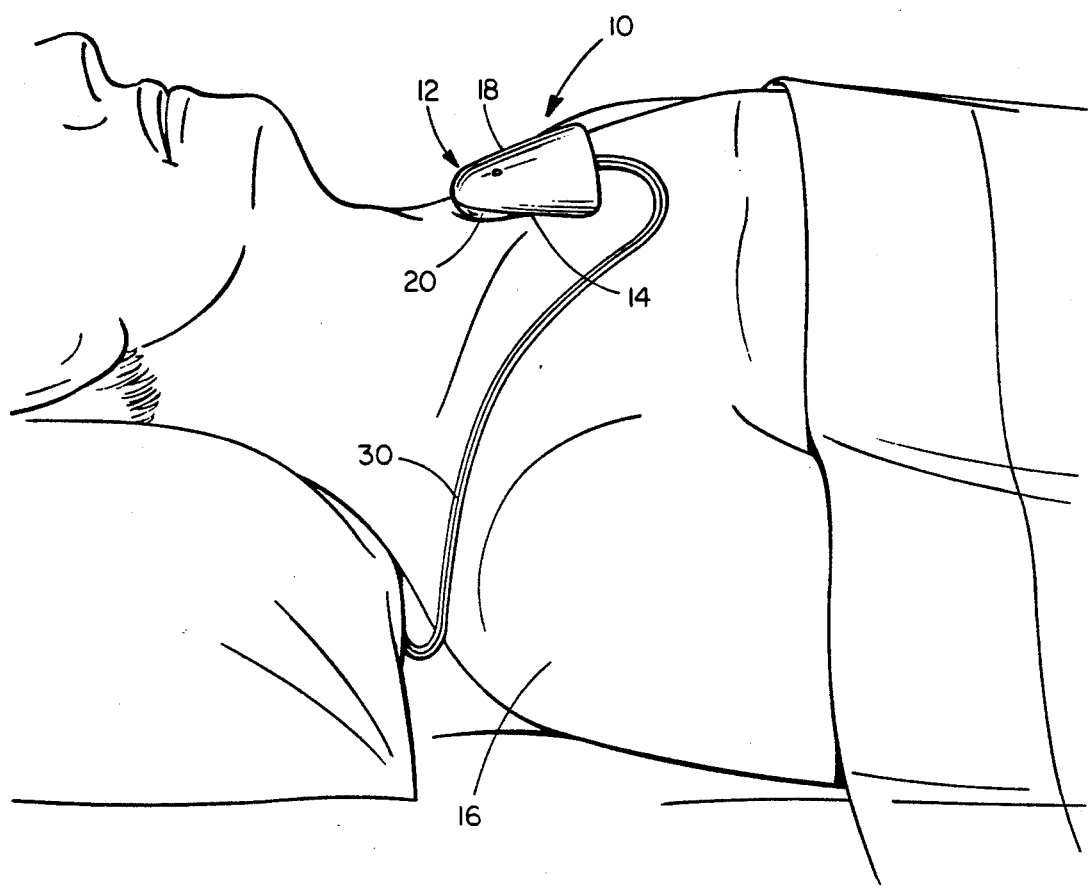
FIG. 1 is a perspective view of the apparatus of the present invention associated with the suprasternal fossa of a human.
Figure 2:
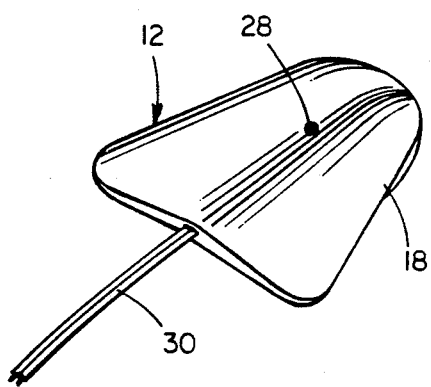
FIG. 2 is a perspective view of the transducer.

Referring specifically to the drawings, the apparatus for noninvasive measuring of changes in intrathoracic pressure and upper airway resistance in humans during sleep is generally designated by reference numeral 10 and includes a transducer 12 associated with the suprasternal fossa 14 of a human 16. The transducer 12 includes a rigid hollow housing 18 of plastic or similar material that is provided with a flexible resilient diaphragm 20 of rubber or similar material forming a closure and base for the housing. The shape of the housing 18 may vary but preferably is of a shape and size that it can be easily handled and secured in position with the diaphragm aligned on the suprasternal fossa of the human.

Figure 3:
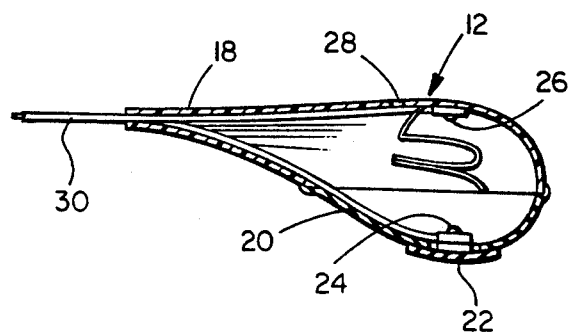
FIG. 3 is a sectional view illustrating the relationship of the components of the transducer.

The diaphragm is anchored to the skin surface of the suprasternal fossa by a replaceable hydrophilic gel-adhesive patch 22 that is secured to the external surface of the diaphragm by which movement of the skin surfaces causes a corresponding movement of the diaphragm. A photodiode 24 is mounted on the inner surface of the diaphragm 20 in opposed relation to the patch 22 with movement of the diaphragm causing corresponding movement of the photodiode 24. A light 26 in the form of a light emitting diode (LED) is mounted stationarily in the housing 18 in a fixed predetermined spaced and aligned facing relation photodiode 24 as illustrated in FIG. 3 which establishes a reference datum output voltage with movement of the photodiode 24 in relation to the LED 26 in response to movement of the skin surface of the suprasternal fossa causing variation in output voltage generated by the photodiode 24 which is a function of light intensity. A vent opening 28 is provided in the housing adjacent to LED 26 to eliminate any pressure build up in the housing due to movement of the diaphragm. Electric conductors 30 are provided to supply electrical energy to the LED and to connect the signal from the transducer to differential AC amplifier or a DC amplifier input to an indicator means to measure changes in intrathoractic pressure and identify changes in upper airway resistance in humans during sleep.

The foregoing is considered as illustrative only of the principles of the invention. Further, since numerous modifications and changes will readily occur to those skilled in the art, it is not desired to limit the invention to the exact construction and operation shown and described, and accordingly, all suitable modification and equivalents may be resorted to, falling within the scope of the invention.

What I claim as new is as follows:

1. An apparatus for measuring changes in intrathoracic pressure and upper airway resistance in humans during sleep comprising a transducer providing a signal output indicating movement of the skin surface of the suprasternal fossa that is a function of changes in intrathoracic pressure, said transducer including a rigid hollow housing adapted to be mounted stationarily in overlying relation to the suprasternal fossa, a flexible resilient diaphragm connected to and forming a closure and base for said housing in facing relation to the suprasternal fossa, means on said diaphragm for bonding a portion of the diaphragm to the skin surface of the suprasternal fossa, a photodiode mounted on said diaphragm within said housing for movement in response to movement of the skin surface, and a light source mounted stationarily within the housing in facing relation to the photodiode to vary output voltage by the photodiode during movement of the photodiode toward and away from the light source corresponding to the movement of the skin surface of the suprasternal fossa, thereby providing a signal which correlates with changes in intrathoracic pressure and upper airway resistance in humans during sleep.

2. The apparatus as defined in claim 1 wherein said means on said diaphragm for bonding to the skin surface includes a replaceable hydrophilic gel-adhesive patch mounted on the diaphragm and adhesively bondable to the skin surface of the suprasternal fossa.

3. The apparatus as defined in claim 2 wherein said light source is a light emitting diode oriented a predetermined distance from the photodiode to establish a reference datum output voltage before movement of the photodiode in response to movement of the skin surface of the suprasternal fossa.

* * * * *